United States Patent [19]

Wallstén et al.

[11] Patent Number: 5,061,275
[45] Date of Patent: Oct. 29, 1991

[54] SELF-EXPANDING PROSTHESIS

[75] Inventors: Hans I. Wallstén, Denens; Christian Imbert, Mézières, both of Switzerland

[73] Assignee: Medinvent S.A., Lausanne, Switzerland

[21] Appl. No.: 456,611

[22] Filed: Dec. 29, 1989

Related U.S. Application Data

[63] Continuation of Ser. No. 33,686, Apr. 3, 1987, abandoned.

[30] Foreign Application Priority Data

Apr. 21, 1986 [SE] Sweden .................................. 8601827

[51] Int. Cl.⁵ .............................................. A61F 2/06
[52] U.S. Cl. ....................................................... 623/1
[58] Field of Search .................... 623/1, 10, 11, 16, 2, 623/66

[56] References Cited

U.S. PATENT DOCUMENTS

| 1,920,495 | 8/1933 | Brown et al. | 140/7 |
| 4,106,129 | 8/1978 | Carpenter et al. | 623/2 |
| 4,655,771 | 4/1987 | Wallsten et al. | 623/1 |
| 4,743,251 | 5/1988 | Barra | 623/1 |

FOREIGN PATENT DOCUMENTS 2135585  3/1986  United Kingdom .................... 623/1

Primary Examiner—David J. Isabella
Attorney, Agent, or Firm—Burns, Doane, Swecker & Mathis

[57] ABSTRACT

A resilient, elastic self-expanding prosthesis comprising a flexible tubular body, the diameter of which is variable under axial movement of the ends of the body relative to each other, said body being composed of several individual rigid but resiliently flexible thread elements with spring properties each of which extends in helix configuration with the center line of the body as a common axis, a number of elements having same direction of winding but being axially displaced relative to each other crossing a number of elements also axially displaced relative to each other but having the opposite direction of winding to form a braided structure, characterized in that the residual tension of the thread elements as they form the structural elements of the tubular body, at least at the end sections thereof, is such that the diameter of the unloaded helix-shaped thread element, at least at the end sections thereof, when removed from the other elements forming the tubular body is not more than about 60% and preferably at most about 30% greater than the diameter of the said body in an unloaded state; and processes for the manufacture of such self-expanding prosthesis.

30 Claims, 2 Drawing Sheets

SELF-EXPANDING PROSTHESIS

This application is a continuation of application Ser. No. 033,686, filed Apr. 3, 1987, now abandoned.

The present invention relates to an elastic, self-expanding prosthesis comprising a flexible tubular body, the diameter of which is variable under axial movement of the ends of the body relative to each other. The invention also covers processes for the manufacture of such self-expanding prosthesis.

Self-expanding prostheses are previously known, for example the one described in British patent 21 35 585. This known prosthesis comprises a flexible tubular body which is composed of several individual rigid but flexible thread elements having spring properties. Each thread element extends in coil configuration with the center line of the body as a common axis, a number of elements having the same direction of winding but axially displaced relative to each other crossing a number of elements also axially displaced to each other but having the opposite direction of winding. These elements suitably form a braided configuration which by means of suitable members can be implanted in a radially contracted condition in for example blood vessels, urinary tracts, bilious tracts, gorges, or other difficulty accessible positions so that it after self-expansion will be fixed at the implantation site thus providing permanent support for the surrounding walls of the vessel.

As is clear from the above-mentioned British patent specification the crossing thread elements are preferably symmetrically arranged in the form of a braid. If the known prosthesis shall be used for example for widening a narrow section in a blood vessel the flexible tubular body is suitably inserted arranged in a radially contracted state at the tip of a flexible instrument, for example percutaneously in a blood vessel. The device is then transluminally transferred to the relevant narrow section of the blood vessel, and the tubular body is then allowed to expand and in a radially expanded state it is released from the instrument so that it remains at the implantation site under self-fixation and the instrument can be removed. In this connection it is essential that the diameter of the body in an unloaded and expanded state has been chosen somewhat larger than the inner diameter of the vessel. This results in a certain permanent pressure or engagement against the inner wall of the vessel which pressure has to be sufficiently large to keep the previous restriction open at the same time as an effective self-fixation will be obtained. In certain cases it has been found suitable first to widen the restriction by angioplasty by means of a so called balloon catheter, the prosthesis being then implanted at the widened position by means of the technique described above.

From a practical point of view prosthesis having self-fixating properties have been found to be preferred, i.e. the tubular body should itself possess such property that it essentially from its own power takes an expanding position at the implantation site. The thread elements constituting the flexible tubular body should therefore be made of a material possessing rigidity and good spring properties in addition that it shall also, of course, be medicinally acceptable. Conceivable materials are metals or metal alloys and certain composite materials and possibly also plastic materials.

As is also clear from the above-mentioned British patent specification the thread elements are preferably built up as monofilaments, i.e. they consists of single thread elements. Such self-expanding prosthesis may also be designed in the form of a graft, the self-expanding thread element skeleton described above forming together with some form of porous layer or sleeve imparting the desired porosity to the tubular body.

A prosthesis of the type described above is suitably manufactured starting from a tubular braid manufactured in a braiding machine known per se wherein usually a number of bobbins, each one containing its thread element, are movably arranged in a ring about a center, so that each bobbin can rotate about its own axis in connection with dewinding the respective thread elements, at the same time as the bobbins are moved about in a zig-zag-shaped circular movement about this center. A number of bobbins are arranged in the same manner in a ring but are moved in a zig-zag-shaped circular movement in the opposite direction in relation to the first-mentioned group of bobbins. The braid is suitably deposited around a tubular axis in the center of the machine, and the thread elements can form different braiding patterns, i.a. depending on how the bobbins are brought to rotate. Tubular prosthesis of a suitable length can then be severed from the manufactured tubular braid.

In practice it has been found that in the practical use of prosthesis of the type described above it is necessary for several reasons that the thread elements forming the tubular body have a dimension which is as small as possible but which at the same time provides for the said necessary force against the wall of the vessel so that the tubular body obtains a small wall thickness so as not to accomodate too much space when for example implanted in fine blood vessels so that a too large reduction of the flow area for the blood will result. This is particularly important with prostheses of a relatively small diameter, for example for use for implantation into the coronary vessels of the heart. Moreover, a small dimension of the thread elements is essential in those cases where one wishes to obtain a high expansion capacity of the prosthesis, i.e. a high ratio between the prosthesis in an expanded state in relation to the prosthesis in a radially contracted state. Another reason as to why small dimensions of the thread elements are desirable is the fact that the prosthesis in a contracted state shall be accommodable in an implantation device of small diameter, for example for percutaneous implantation. Finally, small thickness of the thread elements is an important advantage from a biological point of view, since the prosthesis built up from fine thread elements in an implanted state substantially facilitates coverage of the prosthesis with a layer of natural cells which in a blood vessel prevents the risk for thrombosis. For this reason it has been found that the thread elements must be made of a flexible, rigid, resilient material, for example a spring steel, a spring alloy or the like, the rigidity of the material in combination with its spring properties being of an essential importance. However, it has been found that it is in practice coupled with great difficulties to make a self-expanding prosthesis starting from a material of such properties.

Thus, it has been found that when a prosthesis of a suitable length is severed from a tubular braid made of a material of the desired properties the resulting ends either bend outwardly or possibly turn inwardly against the center of the prosthesis. For this reason such a prosthesis is unuseful for the intended medical purpose. The outwardly extending ends may after implantation of the prosthesis in for example a blood vessel perforate the walls of the blood vessel. On the other hand thread ends pointing inwardly towards the center of the prosthesis may cause thrombosis in the blood vessel. Even if in certain cases a length of prosthesis cut from a tubular braid may have ends which per se could be useful the inherent rigidity of the thread elements means, however, that handling of the prosthesis is quite difficult or even impossible, since the necessary handling in connection with placing the prosthesis in the implantation instrument and in connection with the implantation results in causing disorder of the thread element ends making the prosthesis useless.

The problem has been touched upon in the above-mentioned patent application and therein there is suggested as a solution to the problem welding the thread element ends together in pairs. However, in practice it has been found that this measure does not give the desired effect but that it reduces the elasticity of the prosthesis by rigidifying the ends of the prosthesis and also further accentuation of the risk of penetration of the wall of the vessel. Moreover, said measure constitutes a significantly increased productional cost.

The present invention has for its purpose to provide new technique whereby the problem is eliminated or at any rate substantially reduced.

For this purpose there is thus provided through the invention an elastic, self-expanding prosthesis, the supporting construction of which includes a flexible tubular body which is composed of a plurality of individual rigid but elastically flexible thread elements having spring properties. The tubular body is designed such that the remaining tension of the thread elements in the state in which they constitute supporting elements in the tubular body, at least at the end sections of the body are adjusted so that diameter of an unloaded helix-shaped thread element, at least at its end sections, when removed from the other elements forming the tubular body is not more that about 60% larger than the diameter of said body in an unloaded condition. By the diameter of the thread element there is meant in the present context the diameter of the cylinder within which the helix-shaped thread element can be considered to be inscribed.

As previously indicated the thread elements should be made of a medicinally acceptable material and in addition possess the springiness and strength required in order that the tubular body built up from the elements shall by its own force keep the restriction open and/or give a good self-fixation when implanted at the same time as the thread elements involved have as small a dimension as possible. In order that these requirements shall be met it is suitable that the material of which the thread elements are made has a high energy storage capacity $$\left(\frac{\sigma_y^2}{E}\right)$$

of at least about 5N/mm² and that it has a high modulus of elastiticy $E_E$ (Young) which is at least about 100.000N/mm². Particularly preferred materials have an energy storage capacity of at least about 12N/mm² and a modulus of elasticity $\underline{E}$ which is at least about 150.000N/mm². In the expression for the energy storage capacity $\sigma_y$ means the yield strength in N/mm² and $\underline{E}$ is the modulus of elasticity according to Young also in N/mm².

In order to further facilitate the solution of the problem indicated above which underlies the present invention it is preferred that at least one of the thread elements at each crossing site is deformed in such a manner that it at least partly encloses the other thread element. When using thread elements of circular cross section the expression "at least partly circumscribes" but instead of point contact between crossing thread elements line contact would be obtained. The meaning of the expression in question will be further explained in connection with specific examples described below.

The deformation of the outer thread element at each crossing site can be constituted by a breaking over the inner thread element at the area of contact between the two elements.

In connection with the presentation of the contents of British patent 21 35 585 it has been previously indicated that the tubular body is preferably symmetrically designed and built up from monofilaments. This means in other words that each thread element of the tubular body extends alternatingly radially inside and radially outside the crossing thread elements at the respective crossing points, the number of thread elements in one rotational direction being the same as the number of thread elements in the other rotational direction. In the following this configuration will be called "one above-/one below".

The deformation of at least the outer thread element at each crossing site as described above results in the important advantage that relative sliding movement between the thread elements will be prevented or at any rate made quite difficult, and this in turn means that the solution of the above-indicated problem of the outward bending of the thread ends will be further facilitated. Alternative deformation techniques are conceivable, and another example is one where both thread elements at each crossing site are deformed in the opposite direction relative to each other. The deformation may also be constituted by flattening of the juxtaposed surfaces of crossing thread elements at the crossing site. It has also been surprisingly found that by using the above-mentioned deformation there is also gained the advantage that the disturbing tension of the thread elements is reduced so that if a thread element is removed from the prosthesis it has a helix shape of largely the same pitch as when it was part of the prosthesis, i.e. by the deformation one can also remove a great part of the tensions.

It has been previously indicated that for providing the desired function of the prosthesis the thread elements shall be made of a medicinally acceptable, flexible and rigid resilient material. Many different materials are conceivable but the majority of materials of satisfactory properties are found among the group metals and metal alloys. Particularly preferred are alloys of austenitic strainhardening type, particularly such materials that can be hardened by heating at moderate temperatures. As particularly preferred materials there may be mentioned alloys substantially based on cobolt, chromium, nickel and molybdenum, the alloying residue being iron. As an example of the latter type of materials there may be mentioned alloys containing about 40% cobolt, about 20% chromium, about 16% nickel and about 7% molybdenum. Specific examples of the latter type of alloys are Elgiloy ® and Phynox ®.

In order to further improve the radial stability and self-fixation of the implanted prosthesis it is suitable that the axially directed angle α between crossing elements is greater than about 90° and preferably greater than about 100° of the unloaded prosthesis. It should be observed that the deformation of the thread elements in connection with the crossing sites means that the relative rotational movement between the respective thread elements at each crossing site will not be prevented but can take place at low friction.

According to another aspect of the invention it has been found that in certain cases, particularly in prostheses of small diameter and built up of fine thread elements, it is preferred to design the body so that at its ends in an unloaded condition it widens conically outwardly to a diameter which is grater than the diameter of the rest of the body. The conical widening outwardly can suitably be to a diameter which is at most about 20% greater than the diameter of the body in the intermediate section. The reason why this conical widening of the end sections of the prosthesis results in substantial advantages is the fact that in practice it has been found that the ends of the prosthesis at radial compression of same are subjected to a greater reduction of the diameter than the rest of the body. Since the prosthesis is intended to be implanted in a vessel of somewhat smaller diameter than the prosthesis has in an unloaded state the prosthesis when implanted will therefore obtain a substantially constant diameter across its full length. The desired conicity at the ends can suitably be obtained by adjusting the remaining tension of the thread elements or a selected deformation at the crossing sites.

In order to obtain a prosthesis with filtering function it may optionally be suitable to design at least one end of the body with a diminishing diameter, whereby it can serve as a filter when applied. According to yet another aspect of the invention the prosthesis can comprise extra threads of other materials in order that the prosthesis shall obtain the desired porosity. It may in this case also function as a so called graft.

The previously described deformation of the thread elements at the crossing sites can be obtained in several ways. The invention also relates to processes for the manufacture of the prosthesis.

One embodiment of such prosthesis according to the invention recides in the feature that in connection with the braiding operation in a conventional braiding machine known per se the tubular body is braided under application of such tension to each individual thread element that they are permanently deformed and bent over the under-lying thread element at the crossing point. By applying this technique there will be obtained better adaptation of the remaining tension of the thread elements but also better fixation by bending of the crossing thread elements in relation to each other while maintaining flexibility of the prosthesis. The tension applied to each thread element is suitably at least about 20%, for example about 25-50% of the yield strength of the material of said element.

An alternative process according to the invention to provide for deformation of the thread elements in connection with the crossing points is to subject the body after its manufacture to mechanical deformation, so that at least one of the thread elements at each crossing point at least partly circumscribes the other thread element, so that sliding movement between the crossing threads is prevented, whereas rotational movement under low friction between the thread elements at said crossing points will be made possible. Such mechanical deformation can be provided for example by hammering, mechanical or isostatic pressing or blastring. The mechanical deformation obviously mainly results in deformation of the outer thread element at each crossing point so that it a least partially will circumscribe the underlying thread element.

In case that the tubular body is made of a metal alloy this can finally be heat-treated at an increased temperature for the purpose of releasing tension in the braided configuration thereby reducing the remaining tension in the thread elements forming the skeleton of the prosthesis according to the invention. When using an austenitic tension hardening alloy such final hardening can be performed by heat-treatment at a moderately increased temperature, for example within the range between about 400° and 600° C. Such final hardening on the one hand gives further adaptation of the remaining tension of the thread elements, and on the other hand increased yield strength and thereby increased energy storage capacity.

Reverting to the previously mentioned aspect according to the invention consisting in adapting the remaining tension of the thread elements forming the structural element of the tubular body in a preferred manner it may be added that said diameter of an unloaded helix-shaped thread element removed from the other elements forming the tubular body is preferably not more than about 30% greater than the diameter of the said body in an unloaded condition and in particular it will not exceed the diameter of the body by more than about 20%.

It should be observed that the invention is not limited to thread elements of circular cross section. Other cross sections are thus conceivable, such as square, polygonal etc. A circular cross section is, however, preferred from a manufacturing point of view.

The invention will in the following be further described by non-limiting examples in connection to the appended drawing, wherein.

Figure 1:
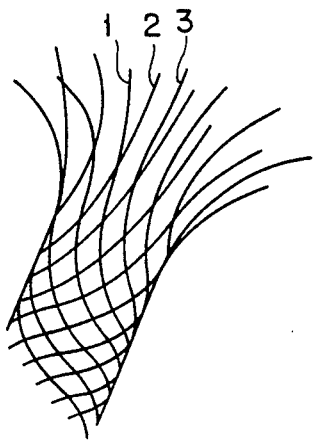
FIG. 1 shows diagrammatically a sideview of a braided tubular body designed in accordance with conventional technique.

FIG. 1 is intended to illustrate a problem forming the basis of the present invention and which is reflected in the fact that a braided prosthesis taken from a tubular braid does not maintain at its ends the configuration corresponding to the construction of the tubular braid. In FIG. 1 there is illustrated an end of a prosthesis, and at the other part of the figure two crossing thread ends have been designated 1 and 2. As is seen the thread ends of the prosthesis generally tend to stick outwardly. This depends on the fact that after severing the tubular braid the ends can slide in relation to each other, the end section of each thread element tending to take its original configuration before the braiding, for example in the form of a straight thread. The thread within the prosthesis extending in helix-shape parallel with thread 1 has been designated 3. Within the prosthesis threads 1 and 3 extend parallel to each other in helix-configuration. As is seen from FIG. 1 the ends of threads 1 and 3 have, however, a tendency to slide so as to be separated from each other at the end of the prosthesis. The problem is accentuated by the fact that prostheses according to the invention are intended while being radially extensively compressed to be arranged in an implantation instrument, wherein the thread elements of the prosthesis form a very small angle to each other. It has been found that the manipulation required for reducing the diameter of the prosthesis with axial elongation of same and the subsequent expansion increases the risk for mutual sliding movement between the thread ends.

Even if in FIG. 1 there is shown a prosthesis end with thread ends extending outwardly a severed prosthesis end may in certain cases have inwardly extending threads. This is explained by the fact that other tension circumstances prevailed in braiding. However, the problem is of the same nature, since as introductorily already stated it has been found necessary that a braided prosthesis for use in implantation after such implantation should have the shape of a straight cylinder also concerning the ends or possibly a straight cylinder with somewhat outwardly extending ends. A much too big deviation from this shape can have catastrophic results.

By utilizing the technique of the present invention prostheses having a substantially cylindrical shape can be manufactured from braided tubular lengths by the fact that the built in tensions in the thread elements, at least in the end sections of the prosthesis, have been wholly or partly eliminated.

One way of obtaining such release of built in tensions in accordance with the invention is to carry out the deformation of the thread elements in connection with the braiding, suitably against a rigid central tube. This is obtained by increasing the tension in the thread element during braiding by suitable breaking means to such an extent that they during the course of braiding amount to at least about 20% and up to about 60% or preferably about 25–50% of the yield strength. In this manner there will be obtained local deformation at the crossing point between two thread elements.

Figure 2:
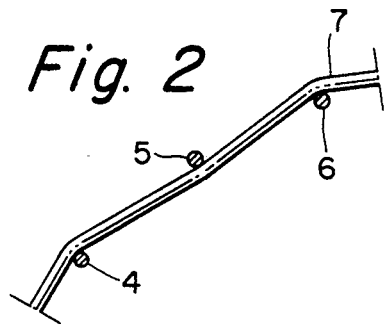
FIGS. 2-7 show details of braided tubular bodies made in accordance with the invention.

In FIG. 2 there is shown a detail of braided prosthesis deformed in this manner, and the figure illustrates three thread elements 4, 5 and 6 extending in parallel, whereas a fourth thread element 7 crosses the thread elements extending in parallel. The braiding patent of the prosthesis is as shown in the figure one thread above and one thread below etc. As is clear from FIG. 2 the thread element 7 rigid per se and made of for example spring steel has been deformed such that it is bent over thread elements 4 and 6 and in this manner it partly circumscribes these thread elements. In view of the plastic deformation in these points thread element 7 will hereby also in released state form a helix shape which closely corresponds to the helix shape of the thread elements when part of the prosthesis. The tendency of the thread elements to take a straighter configuration has in other words been reduced and thus part of the tensions of the thread elements have been eliminated. The same is the case with all thread elements of the prosthesis, and thus also thread elements 4, 5 and 7 have been bent in their respective crossing points with other thread elements extending in parallel with thread element 7. In the example shown in FIG. 2 mainly only the parts of the respective thread elements lying on top of the crossing thread elements as seen in radial direction have been subject to bending.

Through the deformation of the thread elements that will be obtained in the manner described above it is now possible to sever a suitable length of the tubular braid in order to make a prosthesis, the ends of which remain cylindric or almost cylindric, i.e. the risk that the thread ends extend outwardly or bend inwardly has been eliminated. It has also been surprisingly found that such severed prosthesis essentially maintains its cylindric shape also at the end sections in spite of the fact that it is manipulated in different manners, for example in connection with reduction of its diameter to be insertible in a suitable implantation instrument. Even if the tension in the thread elements involved now to a large extent has been reduced one could expect that the thread ends when manipulated would slide in relation to each other at the crossing points and that in this manner there still would be risk that at least some thread ends would extend outwardly or inwardly. It has now been surprisingly found that this is not the case and a contributary cause seems to be the deformation obtained at the crossing points.

Figure 3:
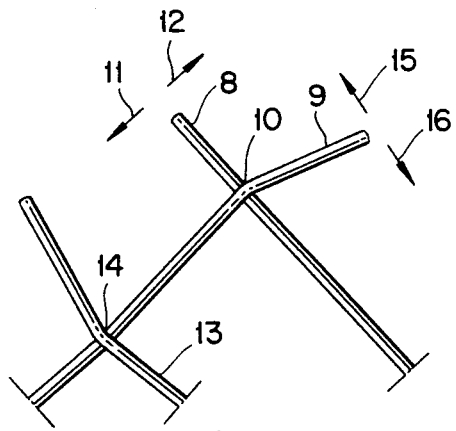

In FIG. 3 there is illustrated in detail how thread end 8 by being in the crossing point 10 partly surrounded by the bent thread 9, is prevented from moving when manipulated in the directions of the two arrows 11 and 12. In a corresponding manner thread element 9, over which the crossing thread element 13 has been bent at the crossing point 14, will be prevented from moving in the directions of arrows 15 and 16, respectively.

Sliding movement between the individual thread ends in the respective crossing points will thus be prevented in this manner, whereas the thread ends, since they have not been fixed at the crossing points, can freely rotate relative to each other at the crossing points in connection with varying of the diameter and length of the prosthesis.

It has been found that the above process is applicable at all thread diameters when manufacturing medicinally useful braided prostheses. The condition is thus that the thread material can be subjected to bending deformation essentially concentrated to the crossing points. The technique described above is particularly applicable when using rather fine thread materials, i.e. for the manufacture of prosthesis having a small diameter. Thus, the technique has been successfully used for the manufacture of prostheses intended for fine blood vessels having a diameter of down to about 2 or 1.5 mm and using threads of spring steel alloy with thread diameters varying between 0.06 mm and 0.17 mm at a total number of thread elements of between 12 and 32.

It may, however, sometimes be desirable to provide for deformation in another manner and for making it possible to manufacture prostheses having cylindric or nearly cylindric ends. Within the scope of this invention it has been found possible either in connection with the braiding or in a separate operation thereafter by means of mechanic deformation, for example hammering, mechanic or isostatic pressing or blastering, to provide an even more pronounced deformation at the crossing points than has been described earlier in conjunction with FIG. 2.

Figure 4:
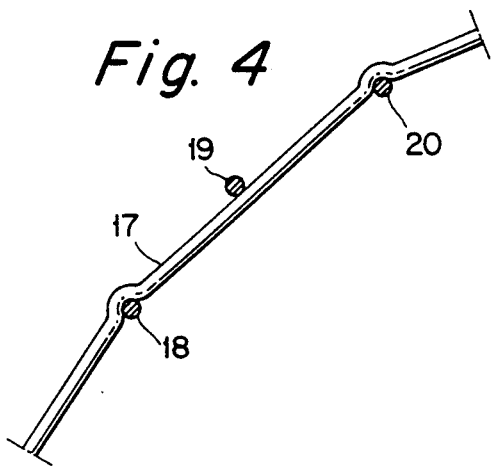

In FIG. 4 there is shown a detail of a prosthesis deformed mechanically at the crossing points by means of pressing. Three thread elements 18, 19 and 20 extending in parallel and shown in section are crossed by a fourth thread element 17. As is clear from the figure thread element 17 has been deformed such that not only has it been bent over the crossing thread elements 18 and 20 but it has also been brought to considerably enclose the last-mentioned thread elements. In the example shown in FIG. 4 the crossing thread elements 18 and 20 are, however, undeformed in connection with the crossing points with thread element 17.

Figure 5:
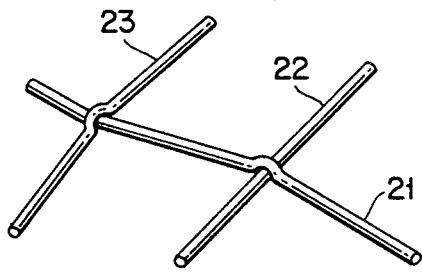

In FIG. 5 there is shown in detail and in perspective a thread element 21 which is crossed by two thread elements 22 and 23 in the configuration above-below taken from the same prosthesis blank as shown in FIG. 4. As is clear from the figure thread blank has been so heavily deformed in the crossing point with thread blank 21 that it has been brought to surround a considerable part of thread blank 21, the latter in the same crossing point being, however, almost intact. At the adjacent crossing point between thread blank 21 and thread blank 22 it is, however, thread blank that has been deformed so as to circumscribe thread blank 22. In this case the detail according to FIG. 5 represents a piece of a prosthesis and seen from the outside, i.e. the deformations in the crossing points extend radially outwardly. The deformation in the embodiment shown in FIG. 5 can be obtained in different ways within the scope of the invention. One way consists in obtaining the deformation in a particular pressing device, wherein the prosthesis has been arranged for example on to a bar having a hard surface. The diameter of the bar is selected in relation to the diameter of the prosthesis so that the prosthesis surrounds the bar with an angle between the crossing helix-shaped thread elements corresponding to the angle that the thread elements shall have in the finished prosthesis. The prosthesis with its bar is placed in a device provided with jamming jaws that can engage from the outside, the bar serving as a support. By rotating the bar with the prosthesis in a suitable manner during the treatment at the same time as possible displacement between each pressing step in a longitudinal direction is made the treatment is continued suitably across the whole surface of the prosthesis by pressing from the outside.

The jamming jaws of the pressing device suitably consist of a softer material than that of which the bar is made. In this manner there will be provided deformation as that shown in FIGS. 4 and 5. As an example of different materials when treating a spring steel there may be mentioned that the central bar suitably can be made from a stainless material, whereas the jaws of the pressing device can be of aluminum of suitable hardness.

It should be clear from FIGS. 4 and 5 that this embodiment gives an even better resistance to sliding between the different thread elements than the embodiment according to FIGS. 2 and 3. In many cases the last-mentioned embodiment is, however, preferred since it results in only one manufacturing step, whereas in other cases the embodiment corresponding to FIGS. 4 and 5 is preferred. This is particularly the case when one uses relatively thick thread diameters, as for example from about 0.10 mm up to about 0.30 mm, which is suitable for prostheses having for example diameters exceeding 8 mm and up to 40 mm and having a number of thread elements exceeding about 24. The method of deformation described above has also successfully been used for the manufacture of prostheses having a number of thread elements of up to 64 threads or more.

Figure 6:
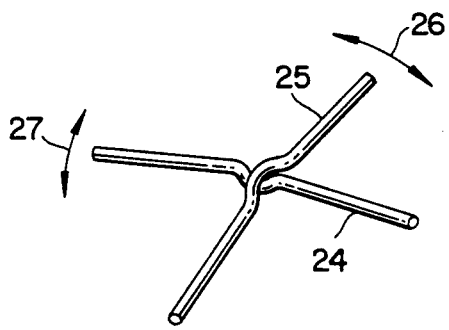

In FIG. 6 there is shown another variant within the scope of the invention. At the crossing point between thread elements 24 and 25 both elements are deformed.

In the figure there is shown a detail of a prosthesis seen from the outside and as seen from the figure the overlying thread element 25 is deformed outwardly in the crossing point as seen a radial direction, whereas thread element 24 is deformed inwardly. It is clear from the figure that in this case lateral sliding movement for the two thread elements 24 and 25 will be prevented, whereas a rotational movement in the crossing point as indicated by arrows 26 and 27 can take place without resistance.

Figure 7:
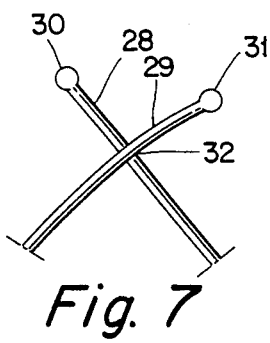

In FIG. 7 there is shown a variant of the embodiment according to FIG. 3. According to this variant each thread end has been provided with a small knob. In the figure this is shown with two crossing thread elements 28 and 29, the ends of which form knobs 30 and 31. In this manner the knobs will reduce the risk that the thread ends slide apart even if they leave their position at crossing point 32. The knobs may be formed in a suitable manner, for example by means of a laser.

Through the different manners of deforming the thread elements as described above two advantages are gained as previously indicated. On the one hand the greater part of the tensions remaining in the thread elements are removed so that each thread element if removed from the prosthesis will take a helix shape with largely the same pitching diameter as when present in the prosthesis. In this manner the risk that the thread ends at the end sections of the severed prosthesis slide sidewise and in this manner bend outwardly or inwardly will be considerably reduced. On the other hand the risk for such sliding movement is further reduced by the simultaneously provided deformations at the crossing points since the deformation counteracts sliding movements mechanically.

Within the scope of the invention there is yet another way to reduce the risks that the end pieces of the prosthesis shall point outwardly or inwardly. It has been found possible by a suitable selection of material for the thread elements to obtain an even better stability of the prosthesis. If one for example selects as thread material a spring steel in the form of an alloy of austenitic type it has been found possible by the methods given above to manufacture within the scope of the invention extremely springing and elastic prostheses of cylindrical shape and with no risk that the ends of the prosthesis shall point outwardly or inwardly. As examples of such austenitic materials giving very good results in this respect there may be mentioned alloys based on cobolt, chromium, nickel and molybdenum and iron. These alloys have been found to have many advantages. There are non-toxic and not cancerogeneous, they are chemically stabile and temperature unsensitive. They have therefore been found to be quite suited as biomaterials, i.e. implanted in the human body they result in a minor reaction or no reaction at all.

Moreover, these materials have excellen springing properties. As example there may be mentioned an alloy having the tradename Phynox ® and another similar alloy Elgyloy ®. These alloys contain about 40% cobolt, 20% chromium, 16% nickel, about 17% molybdenum, the balance being iron.

Another property of these alloys that has been found to be quite valuable in connection with the present invention is the fact that they can be heat-treated at reasonable temperatures resulting in structural conversion. The mechanical properties of these alloys are very good but can be further improved by cold drawing before use. Thus, one can obtain in thread materials of these cold-drawn alloys a tensile strength which is as high as 1500, even up to 2000N/mm² and more.

Such thread material has extremely good springing properties as a spring steel but it is impossible to use in the manufacture of prostheses by for example ordinary braiding. In view of the strong springing properties the material will give thread ends which point strongly outwardly or inwardly and in this manner they are impossible to use when the braided body is severed to form a prosthesis.

It has now, however, been found that this material is particularly suited to use as a prosthesis material. If the thread material, preferably in a cold-drawn state, is first deformed in connection with the prosthesis manufacture in any of the manners described above and which lie within the scope of the invention and then are subjected to subsequent heat-treatment within the temperature range of about 400°-600° C. for a few hours the shape of the already deformed thread elements can be fixed, whereby possible residual tensions after the deformation will be largely removed. At the same time there will be obtained the great advantage that the springing properties of the material by the hardening process are further improved and prostheses are obtained with i.a. a very good expansion capacity. By expansion capacity there is meant the ability of the prosthesis to expand from a small diameter to a large diameter, which is important in order that the prosthesis shall be useful for example for percutaneous implantation. If the diameter of the prosthesis in a freely expanded state is designated $\underline{D}$ and the smallest diameter the prosthesis can have in an implantation instrument is designated $\underline{d}$ the so called expansion number may be expressed as $\underline{D}/\underline{d}$. It has been found that by using certain austenitic alloys, such as Phynox ® one can obtain expansion numbers exceeding 4 and in certain cases 8 and more. In this case the reduction number of the cold-drawn thread should not exceed 70 to 80% to prevent risk for the formation of fissures in the material under compression. On the other hand the reduction number should not be less than 30 to 40%. It is true that the deformation will be facilitated at lower reduction numbers, but the prosthesis will have less springiness and a lower expansion rate. Moreover, there will be increased risk that the implanted prosthesis is deformed by external forces. In view of the fact that this material by the above-mentioned treatment will obtain a very high "springiness" or energy storage capacity prostheses having a very small diameter in a compressed state have been possible to manufacture. This depends on the fact that each individual thread can have a very small diameter but yet result in sufficient force at great expansion. As examples there may be mentioned prostheses having 20 threads with a diameter of 0.07 mm compressed to 1 mm diameter and having the ability of expanding up to 6 mm or more.

Independent of the manner of reducing the tension of the threads it is, as indicated, necessary that only a minor residual tension remains in the respective threads at least in the part forming the end of the prosthesis. The degree of the residual tension can be affected by removing part of a thread from the finished prosthesis. If the tensions in the prosthesis or the end of the prosthesis are largely removed the removed thread element takes the shape of a helix or part of a helix with largely the same pitching diameter as it had when present as a thread element in the prosthesis. A measure on the extent of removal of the tensions is constituted by the diameter of the removed thread element in relation to the diameter of the prosthesis in freely expanded state. It has been found that this ratio should lie between 1.50 and 1.0 but preferably be between 1.3 and 1.0.

It has been found that even if the previously described measures have been taken within the scope of the invention also the type of braiding, the number of thread elements and other factors have an influence on the problem of thread elements pointing outwardly or inwardly. Thus, it has been found that a braiding structure of one thread above and one thread below is to prefer, at least at the ends of the prosthesis. The explanation for this is the fact that the thread ends will be better fixed further out at the end of the prosthesis thus resulting in a shorter free thread end that may point in the wrong direction.

It has also been found that the number of thread elements in relation to the diameter of the prosthesis have influence on the problem with outwardly or inwardly extending thread ends. If for example the number of thread elements at a certain diameter lies below a certain value the thread ends tend to point outwardly. This can be explained by the fact that the number of crossing points are too few in order that sufficient fixation shall be obtained when the prosthesis is manipulated for making same small by compression/elongation for insertion into an implantation instrument. In the same manner there is risk that the thread ends hook on to each other in the corresponding manipulation if the number of thread elements is too great in relation to given prosthesis diameter so that when the prosthesis expands in a vessel certain thread ends are not released from each other which may create problems, in for example a blood vessel. Too many thread elements also stiffen the prosthesis in a compressed state which in certain cases may be a disadvantage when the prosthesis shall pass through bends during implantation.

It has been found that the following relation approximately exists between the prosthesis diameter $\underline{D}$ and the number of thread elements $\underline{n}$ in a prosthesis:

$$\frac{\sqrt{D}}{n} = C$$

wherein $\underline{C}$ is a constant that can be selected between certain extremes. If the diameter $\underline{D}$ is expressed in millimeters $\underline{C}$ should lie between 0.160 and 0.080, a suitable intermediate value being 0.117 when using for example a spring steel thread of an alloy of about 40% cobolt, 20% chromium, 16% nickel, 17% molybdenum, the balance being iron, for diameters from a few millimeters up to about 35 mm.

In the table 1 below there are shown a number of values of prosthesis diameters and the corresponding number of thread elements (optimum and upper and lower limits) calculated from the above formula.

TABLE 1

| | n | | |
|---|---|---|---|
| D mm | $C_2$ min 0.160 | $C_2$ opt. 0.117 | $C_2$ max 0.080 |
| 2.5 | 10 | 14 | 20 |
| 3.5 | 12 | 16 | 23 |
| 4.5 | 13 | 18 | 26 |
| 5.5 | 15 | 20 | 29 |
| 8 | 18 | 24 | 35 |
| 15 | 24 | 33 | 48 |
| 20 | 28 | 38 | 56 |
| 25 | 31 | 43 | 63 |
| 30 | 34 | 47 | 68 |

TABLE 1-continued

| D mm | $C_2$ min 0.160 | $\underline{n}$ $C_2$ opt. 0.117 | $C_2$ max 0.080 |
|---|---|---|---|
| 35 | 37 | 51 | 74 |

An even number of thread elements are suitably selected from the table to enable a braiding pattern of one element above, one element below.

The pressure exerted by the prosthesis after implantation is, of course, dependent on many different factors, i.a. the thread diameter.

Empirically there may be established an approximate relation between thread diameter and prosthesis diameter in order to give suitable pressures. The relation between prosthesis diameter $\underline{D}$ and thread diameter $\underline{d}$ for a thread of a spring steel, for example a spring steel alloy of about 40% cobolt, 20% chromium, 16% nickel and 17% molybdenum, the balance being iron, for a prosthesis intended for implantation in blood vessels or similar tubular organs can be expressed as:

$$\frac{D}{d^2} = C1$$

If $\underline{D}$ and $\underline{d}$ are expressed in millimeters approximate extremes upwardly and downwardly for $\underline{C}$ can be set as 400 and 720, respectively.

Table 2 below also shows values for $\underline{D}$ and $\underline{d}$ for the intermediate $C1 = 555$.

TABLE 2

| D | d max 400 | $\underline{d}$ d med 555 | d min 720 |
|---|---|---|---|
| 2.5 | 0.08 | 0.07 | 0.06 |
| 3.5 | 0.09 | 0.08 | 0.07 |
| 4.5 | 0.11 | 0.09 | 0.08 |
| 5.5 | 0.12 | 0.10 | 0.09 |
| 8 | 0.14 | 0.12 | 0.11 |
| 15 | 0.19 | 0.16 | 0.14 |
| 20 | 0.22 | 0.19 | 0.17 |
| 25 | 0.25 | 0.21 | 0.19 |
| 30 | 0.27 | 0.23 | 0.20 |
| 35 | 0.30 | 0.25 | 0.22 |

As previously indicated it is necessary to use as material for the thread elements materials which are medicinally acceptable, are rigid and have extreme spring properties. Since it is desirable that the wall of the prosthesis is as thin as possible and exerts a certain sufficient pressure against the wall of the vessel at the same time as the prosthesis shall have a high expansion number it has been found that the thread material should have such high "springiness" or energy storage capacity as possible. This can be expressed as $$\frac{\sigma y^2}{E}$$

where $\sigma y$ is the yield strength and E its modulus of elasticity according to Young.

It has been found that the value of the energy storage capacity should exceed $5N/mm^2$ and that values exceeding $12N/mm^2$ are preferred. As examples of such materials there may be mentioned certain stainless alloys, such as stainless steel 316 (18% Cr, 13% Ni, 2,5% Mo) and certain titanium alloys, such as IMI 318 (6% Al, 4% Va). One group of materials that has been found to be extremely suitable is, as already mentioned, certain cobolt alloys, of which cobolt-chromium-nickel-alloys, such as Elgiloy ®, Phynox ® of the composition Co 40%, Cr 20%, Ni 15% and smaller amounts of Mo, Mn, can be mentioned. These materials can, if the prosthesis is manufactured from cold-drawn wire of a reduction grade (cold-work) of 40–70% and after several hours of heat-treatment of the prosthesis in a protected atmosphere reach values on energy storage capacity of $14N/mm^2$ and up to $25N/mm^2$ and more. It has, however, been found that all wire materials of high energy storage capacity are not suitable. Also a very high stiffness and at the same time a small diameter of the wire material will be required. Therefore, the requirement of high energy storage capacity must be combined with a high modulus of elasticity $\underline{E}$. This should exceed $100.000N/mm^2$ but $150.000N/mm^2$ and more is preferred. A great advantage of these materials is, as already mentioned, the fact that one can make prosthesis of fine thread elements and by subsequent heat-treatment the helix shape can be fixed in the individual thread elements of the prosthesis, whereby the tensions are reduced and very high expansion numbers can be obtained with thin walls of the prosthesis of sufficient power.

EXAMPLE

Figure 8:
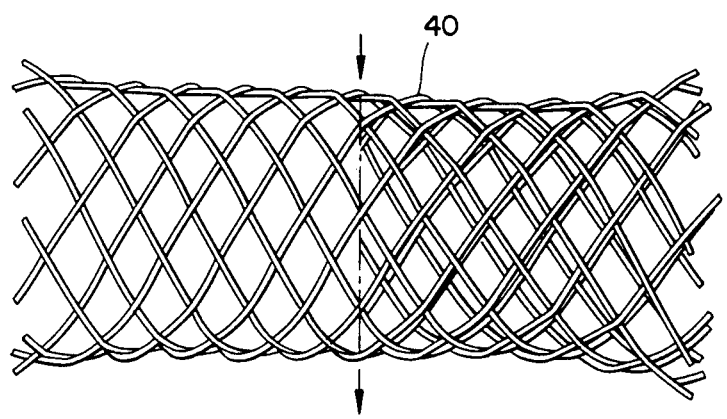
FIG. 8 shows a braided prosthesis designed in accordance with the invention.

In FIG. 8 there is shown a braided prosthesis generally designated 40. The left part of the prosthesis is shown with the lower half covered, whereas the right end part of the prosthesis is shown as a whole. As is clear from the figure prosthesis 40 has a configuration including a central cylindric part, the ends widening somewhat conically outwardly. With the prosthesis in an implanted state, the diameter in relation to the diameter in an unloaded condition being somewhat reduced, the ends will take a position which largely corresponds to the diameter of the central part.

The prosthesis shown in FIG. 8 was manufactured in a braiding machine, wherein the monofilaments consisted of 16 wires, each having a thickness of 0.08 mm. The material was cold-drawn wires of Phynox ®, i.e. an alloy essentially consisting of 40% by weight of cobolt, about 20% chromium, about 16% nickel and about 7% molybdenum having a calculated energy storage capacity $$\left(\frac{\sigma y^2}{E}\right)$$

of about $24N/mm^2$ and a modulus of elasticity $\underline{E}$ (Young) of about $200.000N/mm^2$. The braiding was performed around a central rigid shaft in a braiding pattern of one above/one below.

In order to provide for the necessary deformation in the crossing points there was used a particularly arranged breaking means for each bobbin so that the tension in the braiding was about 20% of the yield strength of the wire. From the braid thus produced a prosthesis was severed which then was subjected to heat-treatment for 3 hours at a temperature of 520° C. in a vacuum oven. The finished prosthesis had a diameter of 3.5 mm in expanded state.

Figure 9:
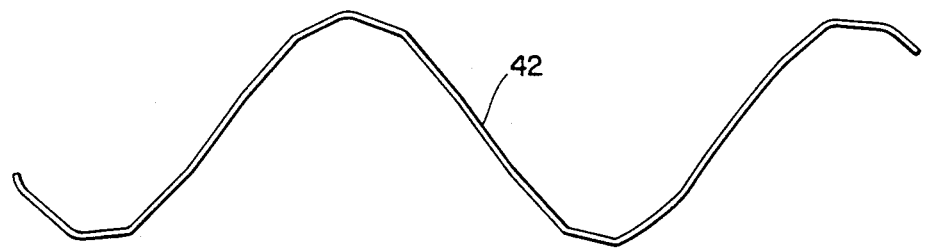
FIG. 9 shows a separate thread element removed from the prosthesis of FIG. 8.

From similar prosthesis severed from the same braid there was removed a thread element as shown in FIG. 9. One can clearly distinguish the fact that this thread element has been broken at the crossing points, which is clear also from FIG. 8. The remaining tension in the thread element corresponded to about 40% greater diameter of the free thread element than of the prosthesis.

The first prosthesis was positioned by means of compression and simultaneous axial extension over the tip of a small flexible implantation instrument provided with a central channel to enable i.a. insertion of a so called guide wire in the channel to facilitate insertion of the prosthesis. The prosthesis was in compressed state surrounded by a thin plastic tube belonging to the tip of the instrument. The total diameter of the compressed prosthesis was 1.2 mm and the corresponding dimension of the tip of the instrument with the enclosed prosthesis was 1.5 mm.

A so called guide catheter having an inner diameter of 1.6 mm was percutaneously inserted into the femoral artery of a dog up to the heart and so that the opening of the catheter was located at the inlet side of the heart coronary vessel arteries. The flexible instrument with prosthesis and guide wire was moved inside the catheter up to the coronary vessel arteries. Then, the guide wire was inserted from the outside into one of the main coronary arteries scientifically called LAD having a diameter of 3 mm. Then the instrument was put from the outside inwardly so that its tip followed the guide wire in to LAD.

A the proper location the prosthesis was released from the outside and expanded and in view of the expansion forces thereof it supported the wall of the vessel and was held attached thereto. The instrument, guide wire and catheter were the removed. The implantation was followed up by exray and contrast liquid and the whole procedure took about a quarter of an hour.

Subsequent control and autopsy showed that after four weeks the implanted prosthesis was totally covered with a glossy layer of bodyly cells largely consisting of endothelium protecting against the formation of trombosis.

The aera of the wall of the artery wherein the prosthesis was ingrown was elastic and showed no reactions whatsoever in relation to the surrounding tissue.

Figure 10:
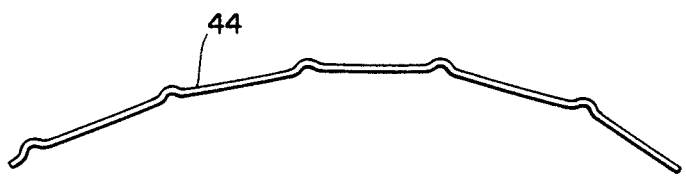
FIG. 10 shows a section of a thread element taken from a prosthesis which after braiding has been subjected to mechanical deformation.

In FIG. 10 there is shown a section of a thread element 44 removed from the prosthesis which after braiding has been subjected to mechanic deformation by pressing as previously described. From the figure it is clear that the crossing sections had not only been broken but also deformed to further enclose the underlying crossing thread element.

Figure 11:
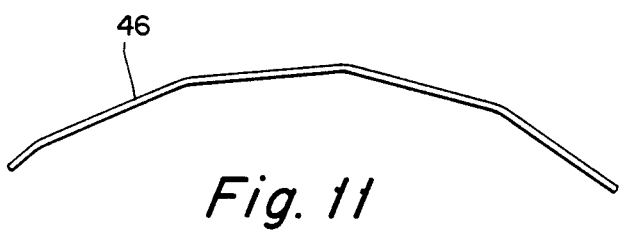
FIG. 11 shows a section of a thread element removed from the prosthesis where thread elements have been bent during braiding.

In FIG. 11 there is shown a corresponding section of a thread element 46 taken out from a prosthesis where the thread elements had been broken only in connection with the braiding. The figure shows clearly the breaking points in connection with the crossing points of the thread element 46 in relation to the crossing thread element.

Even if the present invention has been described above in conjunction with certain specific embodiments it should be observed that the invention is in no way limited hereto. Thus, other types of materials than the above-mentioned may be used as long as they meet the criteria concerning energy storage capacity and elasticity modulus. Alternative procedures for the removal of remaining tensions in the thread elements are conceivable and the invention is only limited to the scope as defined in the appended patent claims.

We claim:

1. A resilient, elastic self-expanding prosthesis comprising a flexible tubular body defining a diameter and terminating at opposite ends, the diametr of which is variable under axial movement of ends of the body relative to each other, said body comprising of several individual resiliently flexible thread elements with spring properties each of which extends in helix configuration relative to a center line of the body as a common axis, a plurality of said thread elements having a common direction of winding but being axially displaced relative to each other and crossing a further plurality of said thread elements also axially displaced relative to each other but having a common opposite direction of winding to form a braided structure, the crossing of the elements occurring at an area of contact between the elements, wherein tension of the thread elements as they form the structural elements of the tubular body, at least at end sections thereof, is such that the diameter of the individual unloaded helix-shaped thread element is not more then about 60% greater than the diameter of said body in an unloaded state, whereby the body at the ends thereof in an unloaded condition is conically widened up to a diameter about 20% greater than the diameter of a main portion of the body.

2. A prosthesis according to claim 1, wherein the thread elements are made of a bio-compatible material having an energy storage capacity of at least about $5N/mm^2$ and a modulus of elasticity which is at least about 100.000 $N/mm^2$.

3. A prosthesis according to claim 1, wherein said thread elements include at least an outer thread element at each said area of contact deformed by being bent over an inner thread element at the area of contact between the two elements.

4. A prosthesis according to claim 1, wherein each thread element extends alternatingly radially outwardly and radially inwardly of the crossing thread elements at the area of contact between the two elements, the number of thread elements of one direction of winding being the same as the number of thread elements of the other direction of winding.

5. A prosthesis according to claim 1, wherein both thread elements at the area contact are oppositely deformed.

6. A prosthesis according to claim 5, wherein the juxtaposed surfaces of crossing thread elements at the area of contact are deformed.

7. A prosthesis according to claim 1, wherein the thread elements are a metallic material.

8. A prosthesis according to claim 7, wherein the thread elements are an austenitic steel strain hardened alloy.

9. A prosthesis according to claim 8, wherein said steel alloy comprises cobalt, chromium, nickel and molybdenum.

10. A prosthesis according to claim 9, wherein said alloy contains about 40% cobalt, about 20% chromium, about 16% nickel and about 17% molybdenum.

11. a phosthesis according to claim 1, wherein an axially directed angle ($\alpha$) between crossing elements is greater than about 90%.

12. A prosthesis according to claim 1, comprising additional material interspersed with said thread elements to provide for desired porosity of the prosthesis.

13. A prosthesis according to claim 2, wherein at least one of the thread elements at each said area of contact thereof is deformed so as to embrace the other thread element.

14. A prosthesis according to claim 8, wherein said steel alloy comprises cobalt, chromium, nickel and molybdenum.

15. A resilient, elastic self-expanding prosthesis comprising a flexible tubular body defining a diameter and terminating at opposite ends, the diameter of which is variable under axial movement of ends of the body relative to each other, said body comprising of serveral individual resiliently flexible thread elements with spring properties each of which extends in helix configuration relative to a center line of the body as a common axis, a plurality of said thread elements having a common direction of winding but being axially displaced relative to each other and crossing a further plurality of said thread elements also axially displaced relative to each other but having an opposite direction of winding to form a braided structure, the crossing of the elements occurring at an area of contact between the elements, wherein residual tension of the thread elements as they form the structural elements of the tubular body, at least at end sections thereof, is such that the diameter of the individual unloaded helix-shaped thread element, at least at the end sections thereof, is not more than about 60% greater than the diameter of said body in an unloaded state, at least one of the thread elements at each said area of contact being deformed so as to embrace the other thread element, whereby the body at the ends thereof in an unloaded condition is conically widened up to a diameter of about 20% greater than the diameter of a main portion of the body.

16. A resilient, elastic self-expanding prosthesis comprising a flexible tubular body defining a diameter and terminating at opposite ends, the diameter of which is variable under axial movement of ends of the body relative to each other, siad body comprising several individual resiliently flexible thread elements with spring properties each of which extends in helix configuration relative to a center line of the body as a common axis, a plurality of said thread elements having a common direction of winding but being axially displaced relative to each other and crossing a further plurality of said thread elements also axially displaced relative to each other but having an opposite direction of winding to from a braided sturcture, alternating inner and outer threads the crossing of the elements occurring at an area of contact between the elements, wherein tension of the thread elements as they form the structural elements of the tubular body, at least at end sections thereof, is such that the diameter of the individual unloaded helix-shaped thread element, at least at the end sections thereof, is not more than about 60% greater than the diameter of said body in an unloaded state, and both thread elements at the area of contact are oppositely deformed, whereby the body at the ends thereof is an unloaded condition is conically widened up to a diameter about 20% greater than the diameter of a main portion of the body.

17. A prosthesis according to claim 15, wherein the thread elements are made of a bio-compatible material having an energy storage capacity of at least about 12 N/mm$^2$ and a modulus of elasticity which is at least about 150,000 N/mm$^2$.

18. A prosthesis according to clim 15, wherein said thread elements include at least an outer thread element at each said area of contact deformed by being bent over an inner thread elements at the area of contact between the two elements.

19. A prosthesis according to claim 15, wherein each thread element extends alternatingly radially outwardly and radially inwardly of the crossing thread elements at the area of contact between the two elements, the number of thread elements of one direction of winding being the same as the number of thread elements of the other direction of winding.

20. The prosthesis according to claim 15, wherein both thread elements at the area of contact are oppositely deformed.

21. The prosthesis according to claim 20, wherein the juxtaposed surfaces of crossing thread elements at the area of contact are deformed.

22. The prosthesis according to claim 15, wherein the thread elements are an austenitic steel strain hardened alloy.

23. The prosthesis according to claim 22, wherein said steel alloy comprises cobalt, chromium, nickel and molybdenum.

24. The prosthesis according to claim 16, wherein at least one of the thread elements at each said area of contact is deformed so as to embrace the other thread element.

25. The prosthesis according to claim 16, wherein said thread elements include at least an outer thread element at each area of contact deformed by being bent over an inner thread element at the area of contact between the two elements.

26. The prosthesis according to claim 16, wherein each thread element extends alternatingly radially outwardly and radially inwardly of the crossing thread elements at the area of contact between the two elements, the number of thread elements of one direction of winding being the same as the number of thread elements of the other direction of winding.

27. The prosthesis according to claim 16, wherein the juxtaposed surfaces of crossing thread elements at the area of contact are deformed.

28. The prosthesis according to claim 16, wherein the thread elements are an austenitic steel strain hardened alloy.

29. The prosthesis according to claim 28, wherein said steel alloy comprises cobalt, chromium, nickel and molybdenum.

30. a resilient, elastic self-expanding prosthesis comprising a flexible tubular body defining a diameter and terminating at opposite ends, the diameter of which is variable under axial movement of ends of the body relative to each other, said body comprising serveral individually resiliently flexible thread elements with spring properties each of which extends in helix configuration relative to a center line of the body as a common axis, a plurality of said thread elements having a common direction of winding but being axially displaced relative to each other and crossing a further plurality of said thread elements also axially displaced relative to each other but having a common opposite direction of winding to form a braided structure, the crossing of the elements occurring at an area of contact between the elements wherein tension of the thread elements as they form the structural elements of the tubular body, at least at end sections thereof, is such that the diameter of the individual unloaded helix-shaped thread element is not more than about 60% greater than the diameter of said body in an unloaded state, said body having at least one end with a diameter which decreases with respect to a main portion of the body, defined between the ends of the body, so as to act as a filter.

* * * * *